United States Patent [19]
Takemoto et al.

[11] Patent Number: 6,010,733
[45] Date of Patent: *Jan. 4, 2000

[54] ASPARTYLAMIDE DERIVATIVES AND SWEETENERS

[75] Inventors: Tadashi Takemoto; Yusuke Amino; Ryoichiro Nakamura, all of Kawasaki, Japan

[73] Assignee: Ajinomoto Co., Inc., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/782,949

[22] Filed: Jan. 13, 1997

[30] Foreign Application Priority Data

Jan. 12, 1996 [JP] Japan ................................. 8-003651
Apr. 1, 1996 [JP] Japan ................................. 8-078718
Nov. 1, 1996 [JP] Japan ................................. 8-291501

[51] Int. Cl.⁷ ....................................................... A23L 1/236
[52] U.S. Cl. ............................. 426/548; 562/448; 562/508; 562/564
[58] Field of Search ........................... 562/448, 508, 562/564; 426/548

[56] References Cited

U.S. PATENT DOCUMENTS 3,803,223 4/1974 Mazur et al. .
4,423,029 12/1983 Rizzi .

FOREIGN PATENT DOCUMENTS 0 203 540 12/1986 European Pat. Off. .
0 255 343 2/1988 European Pat. Off. .
0 310 341 4/1989 European Pat. Off. .
1 906 048 8/1969 Germany .

OTHER PUBLICATIONS

Journal of Medicinal Chemistry, vol. 13, No. 6, pp. 1217–1221, (1970), Robert H. Mazur, et al., "Structure–Taste Relationships of Aspartic Acid Amides".

Tetrahedron Letters, vol. 35, No. 37, pp. 6891–6894, (1994), Yashifumi Yuasa, et al., "The Sweetness and Stereochemistry of L–Aspartyl–Fenchylaminoalcohol Derivatives".

*Primary Examiner*—Samuel Barts
*Attorney, Agent, or Firm*—Oblon, Spivak, McClelland, Maier & Neustadt, P.C.

[57] ABSTRACT

Novel aspartylamide derivatives such as N-(α-L-aspartyl-(1R,2S,4S)-1-methyl-2-hydroxy-4-phenylhexylamide, N-α-7(N'-3,3-dimethylbutylaspartyl)-(1R,2S,4S)-1-methyl-2-hydroxy-4-phenylhexylamide) and the like, and a sweetener containing the above-mentioned derivatives or salts thereof as an active ingredient, is low-calory and which exhibits a high level of stability, an excellent safety and an excellent sweetness.

13 Claims, No Drawings

ASPARTYLAMIDE DERIVATIVES AND SWEETENERS

BACKGROUND OF THE INVENTION

1. Field of the Invention

The present invention relates to novel aspartylamide derivatives and salts thereof as well as a sweetener containing the same as an active ingredient.

2. Discussion of the Art

In recent years, eating habits have been improved to a high level, and fatness caused by excessive intake of sugar and diseases accompanied by the fatness have been at issue. Therefore, the development of a low-calory sweetener that replaces sugar has been in demand. As a sweetener that has been widely used at present, there is aspartame which is excellent terms of a safety and sweetness properties. However, it involves a problem of a stability. In order to improve the stability and the sweetness intensity, an aspartylamide derivative which is a condensate of aspartic acid and β-amino-alcohol and which is free from an ester linkage was studied. Thus, the compounds described in U.S. Pat. No. 4,423,029, European Patent No. EP 0203540A, J. Med. Chem., 13, 1217 (1970) or Tetrahedron Letters, 35, 6891 (1994) were found. Meanwhile, it is described in French Patent No. 2,697,844 that aspartyldipeptide derivatives in which an alkyl group has been introduced into an amino group exhibits an extremely increased degree of sweetness. However, these compounds do not satisfy the stability.

Problems To Be Solved by the Invention

The present invention is to provide novel aspartylamide derivatives and salts thereof which are obtained by using an easily-obtainable amino-alcohol component and which exhibit a high level of safety and an excellent stability, as well as a low-calory sweetener containing the same as an active ingredient.

Means Taken For Solving the Problems

In order to solve the above-mentioned problems, the present inventors have assiduously conducted investigations with respect to an N-alkyl group and an amino-alcohol component of aspartylamide derivatives, and have consequently found that aspartylamide derivatives represented by the following formula (I) are used as a sweetener which is excellent in terms of sweetness intensity, stability and sweetness properties. This finding has led to the completion of the present invention.

$$R_1—NHC—H(CH_2COOH)CONH—C^2R_2R_3—C^3H(OH)—R_4 \quad (I)$$

wherein $R_1$ represents H, or a saturated, unsaturated, acyclic, and/or cyclic hydrocarbon group having from 1 to 13 carbon atoms;

$R_2$ and $R_3$ each represent H, or a substituent selected from an alkyl group having from 1 to 6 carbon atoms, an alkoxyalkyl group having from 2 to 7 carbon atoms, a hydroxyalkyl group having from 2 to 7 carbon atoms, a phenyl group, and a 2-furyl group, or $R_2$ and $R_3$ taken together with the carbon to which they are attached form a cycloalkyl group containing 3 to 6 carbon atoms;

when $R_1$ is a saturated, unsaturated, acyclic, and/or cyclic hydrocarbon group having from 1 to 13 carbon atoms, $R_4$ represents an alkyl group having from 1 to 12 carbon atoms, or a substituent represented by formula (II) or (III), and when $R_1$ is H, $R_4$ represents a substituent represented by formula (III)

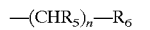  (II)

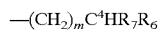  (III)

in which in formula (II)

$R_5$ represents H, or an alkyl group having from 1 to 4 carbon atoms, $R_6$ represents a cyclic group containing up to 10 ring carbon atoms and up to 12 total carbon atoms, which cyclic group is cycloalkyl, cycloalkenyl, lower alkyl substituted cycloalkyl or cycloalkenyl, bicycloalkyl, bicycloalkenyl, or tricycloalkyl, and n represents 0 or 1, and in formula (III)

$R_7$ and $R_8$ each represent H; a cycloalkyl group having from 3 to 4 carbon atoms; an alkyl group having from 1 to 6 carbon atoms; an alkoxyalkyl group having from 2 to 7 carbon atoms; a phenyl group; a phenyl group having a substituent selected from F, Cl, Br, I, a hydroxy group, an alkyl group having from 1 to 6 carbon atoms, an alkoxy group having from 2 to 7 carbon atoms, a cyano group, a nitro group, an acetyl group, an amino group and an acetylamino group in the 2-, 3- or 4-position; a phenyl group having a methylenedioxy group, a trimethylene group or a tetramethylene group in the 2- and 3-positions or in the 3- and 4-positions; a 2-, 3- or 4-pyridyl group; a 2- or 3-furyl group; or a 2- or 3-thienyl group, and m represents 0 or 1; and the $C^1$-configuration is (S), and the $C^2$-, $C^3$- and $C^4$-configurations are (R), (S) or (RS).

MODE OF CARRYING OUT THE INVENTION

The novel aspartylamide derivatives of the present invention are the compounds of formula (I) and salts thereof.

Examples of the salts of the compounds in the present invention include salts with alkali metals such as sodium and potassium; salts with alkaline-earth metals such as calcium and magnesium; salts with amines such as monoethanolamine; salts with inorganic acids such as hydrochloric acid and sulfuric acid; and salts with organic acids such as citric acid and acetic acid.

The aspartylamide derivatives of the present invention can be formed by a usual peptide synthesis method Izumiya et al., Basis of Peptide Synthesis and Experiments thereof, Maruzen, Jan. 20, 1985). That is, desired α-L-aspartylamide can be formed by first condensing an amino-alcohol with L-aspartic acid in which a carboxylic acid in the β-position and an amino group are protected to obtain an amide, and then removing the protective groups, or by first converting L-aspartic acid in which a carboxylic acid in the β-position and an amino group are protected into an active ester, reacting this ester with an amino-alcohol to obtain an amide, and then removing the protective groups. However, the method of forming the compounds in the present invention is not limited thereto.

The N-alkylaspartylamide derivatives can be formed by obtaining an amide of L-aspartic acid having protective groups and an amino-alcohol, then selectively removing the N-protective group, reductively alkylating the resulting compound with an aldehyde [A. F. Abdel-Magid et al., Tetrahedron Letters, 31, 5595 (1990)], and further removing remaining protective group. That is, an amino-alcohol is first condensed with L-aspartic acid in which a carboxylic acid in the β-position and an amino group are protected to obtain an amide, or L-aspartic acid in which a carboxylic acid in the β-position and an amino group are protected is first converted into an active ester, and this active ester is then reacted with an amino-alcohol to obtain an amide. The N-protective group or this protected aspartylamide is selectively removed, the resulting substance is reductively alkylated with an aldehyde and a reducing agent [for example, NaB(OAc)₃H], and the remaining protective group is then removed to give a desired N-alkyl-α-L-aspartylamide. The N-alkyl-α-L-aspartylamide can also be obtained by reductively alkylating the above-obtained α-L-aspartylamide with an aldehyde and a reducing agent (for example, palladium on carbon). However, the method of forming the compounds of the present invention is not limited thereto. The amino-alcohol which is used to produce the compounds of the present invention can easily be obtained from an amino acid as an optically active substance by the method described in the literature [Tetrahedron Letters, by M. W. Holladay et al., 24, 4401 (1983), or Angew. Chem. Int. Ed. Engle., by M. T. Reets et al., 26, 1141 (1987)]. However, the method of forming the amino-alcohol in the present invention is not limited thereto.

As a result of the sensory evaluation, it was found that the compounds of the present invention and the salts thereof have a strong sweetness and their sweetness qualities are similar to that of sugar. For example, the degree of sweetness of N-α-L-aspartyl-(1R,2S,4S)-methyl-2-hydroxy-4-phenylhexylamide was approximately 2,500 times (that of sugar), the degree of sweetness of N-α-L-aspartyl-1R,2S,4R)-1-methyl-2-hydroxy-4-phenylhexylamide was approximately 1,500 times (that of sugar), the degree of sweetness of N-α-L-aspartyl-(1R,2S,4RS)-1-methyl-2-hydroxy-4-phenylhexylamide was approximately 2,300 times (that of sugar), the degree of sweetness of N-α-L-(N'-3,3-dimethylbutylaspartyl)-(1R,2S,4S)-1-methyl-2-hydroxy-4-phenylhexylamide was approximately 5,500 times (that of sugar), the degree of sweetness of N-α-L-(N'-3,3-dimethylbutylaspartyl)-(1R,2S,4R,)-1-methyl-2-hydroxy-4-phenylhexylamide was approximately 3,000 times (that of sugar), the degree of sweetness of N-α-L-(N'-2-ethylbutylaspartyl)-(1R,2S,4S)-1-methyl-2-hydroxy-4-phenylhexylamide was approximately 3,000 times (that of sugar), and the degree of sweetness of N-α-L-(N'-3-methylbutylaspartyl)-(1R,2S,4S)-1-methyl-2-hydroxy-4-phenylhexylamide was approximately 4,000 times (that of sugar).

The half-life (in a phosphate buffer of pH 3 at 70° C.) of N-α-L-aspartyl-(1R,2S,4S)-1-methyl-2-hydroxy-4-phenylhexylamide in an acidic aqueous solution was approximately 289 hours, and it was by far stabler than aspartame (half-life approximately 24 hours).

Further, N-α-L-aspartyl-(1R,2S,4S)-1-methyl-2-hydroxy-4-phenylhexylamide was subjected to a toxicity test in one oral administration (2.0 g/kg) using ICR-strain mice. Consequently, it was found that this compound has no problem with respect to safety.

The structures of the aspartylamide derivatives formed and the results of the sensory evaluation thereof are shown in Table 1.

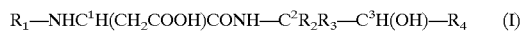

$$R_1\text{—}NHC^1H(CH_2COOH)CONH\text{—}C^2R_2R_3\text{—}C^3H(OH)\text{—}R_4 \quad (I)$$

TABLE 1

Structures of aspartylamide derivatives and degrees of sweetness thereof

| $R_1$ | $R_2$ | $R_3$ | $C^2$-configuration | $C^3$-configuration S:R | $R_4$ | Degree of Sweetness[1] |
|---|---|---|---|---|---|---|
| H | H | Me | R | >5:1 | (S)-2-phenyl-butyl | 2500 |
| H | H | Me | R | >9:1 | (R)-2-phenyl-butyl | 1500 |
| H | H | Me | R | >9:1 | (RS)-2-phenyl-butyl | 2300 |
| H | H | Me | R | 3:7 | (RS)-2-phenyl-butyl | 1000 |
| H | H | Me | R | 3:7 | (R)-2-phenyl-butyl | 800 |
| H | H | Me | R | 7:3 | (RS)-2-phenyl-propyl | 700 |
| H | H | Me | R | 7:3 | (RS)-2-phenyl-3-methoxy-propyl | 100 |
| H | H | Et | R | >9:1 | (RS)-2-phenyl-butyl | 250 |
| H | H | MeCH—(OH) | R | 9:1 | (RS)-2-phenyl-butyl | 100 |
| H | Me | Me | — | 1:1 | (RS)-2-phenyl-butyl | 250 |
| H | H | Me | R | 9:1 | (2)-phenyl-ethyl | 50 |
| 3,3-dimethyl-butyl | H | Me | R | >5:1 | (S)-2-phenyl-butyl | 5500 |
| 3,3-dmethyl-butyl | H | Me | R | >9:1 | (R)-2-phenyl-butyl | 3000 |
| 2-ethylbutyl | H | Me | R | >5:1 | (S)-2-phenyl-butyl | 3000 |
| 3-methylbutyl | H | Me | R | >5:1 | (S)-2-phenyl-butyl | 4000 |
| 3,3-dimethyl-butyl | H | Me | R | >9:1 | cyclohexylmethyl | 100 |
| 3,3-dimethyl-butyl | H | Me | R | 3:7 | cyclohexylmethyl | 750 |

[1] Relative to a degree of sweetness of a 4% sucrose aqueous solution.
[2] The $C^1$-configuration is (S).

When the compounds of the present invention or the salts thereof are used as a sweetener, these compounds may generally be used in combination with other sweeteners.

Having generally described this invention, a further understanding can be obtained by reference to certain specific examples which are provided herein for purposes of illustration only and are not intended to be limiting unless otherwise specified.

EXAMPLE 1

Synthesis of N-α-L-aspartyl-(1R,2S,4S)-1-methyl-2-hydroxy-4-phenylhexylamide

LAH (0.73 g, 19.25 mmols) was suspended in 50 ml, of ether, and the suspension was maintained at 0° C. To this suspension were added 3.44 g (11.0 mmols) of N-methoxy-N-methylcarboxyamide of N,N-dibenzyl-α-D-alanine. The mixture was stirred at 0° C. for 1 hour, and 50 ml of a 1-M potassium hydrogensulfate aqueous solution were added thereto. The reaction solution was extracted twice with 50 ml of ether. The organic layer was washed with 50 ml of a 5% sodium hydrogencarbonate aqueous solution and with a saturated aqueous solution of sodium chloride, and was dried over anhydrous magnesium sulfate. Magnesium sulfate was removed by filtration, and the filtrate was concentrated to obtain 2.76 g (10.9 mmols) of (R)-2-N,N-dibenzylaminopropyl aldehyde.

Magnesium (0.24 g, 9.9 mmols) was suspended in 1 ml of THF, and a solution of 1.41 g (6.6 mmols) of (R)-2-phenylbutyl bromide in 2 ml of THF was added dropwise to the suspension. The reaction solution was stirred at room temperature for 1 hour, and 5 ml of THF were added thereto. The mixed solution was cooled to 0° C. To the reaction solution was added a solution obtained by dissolving 1.37 g (5.5 mmols) of the above-obtained (R)-2-N,N-dibenzylaminopropyl aldehyde in 10 ml of THF, and the mixture was stirred at 0° C. for 1 hour. To this reaction solution were added 50 ml of a saturated aqueous solution of ammonium chloride, and the mixture was extracted twice with 50 ml of ether. The organic layer was washed with 5% sodium hydrogencarbonate and with a saturated aqueous solution of sodium chloride, and was dried over anhydrous magnesium sulfate. Magnesium sulfate was removed by filtration, and the filtrate was concentrated. The residue was purified by PTLC to give 1.46 g (3.77 mmols) of N,N-dibenzyl-(1R,2S,4S)-1-methyl-2-hydroxy-4-phenylhexylamine (2S:2R=>5:1).

N,N-dibenzyl-(1R,2S,4S)-1-methyl-2-hydroxy-4-phenylhexylamine (1.46 g, 3.77 mmols) was dissolved in 25 ml of methanol, and 0.43 ml (7.53 mmols) of acetic acid and 0.6 g of 5% palladium on carbon (water content 50%) were added thereto. The reaction solution was stirred under a hydrogen atmosphere at 50° C. for 16 hours. Subsequently, the catalyst was removed by filtration, and the filtrate was concentrated. To the residue were added 15 ml of a saturated aqueous solution of sodium hydrogencarbonate, and the mixture was extracted twice with 50 ml of methylene chloride. The organic layer was dried over anhydrous magnesium sulfate, and magnesium sulfate was then removed by filtration. The filtrate was concentrated to obtain 0.61 g (2.96 mmols) of (1R,2S,4S)-1-methyl-2-hydroxy-4-phenylhexylamine.

To 30 ml of methylene chloride were added 1.17 g (3.26 mmols) of N-benzyloxycarbonyl-L-aspartic acid-β-benzyl ester and 0.61 g (2.96 mmols) of (1R,2S,4S)-1-methyl-2-hydroxy-4-phenylhexylamine. The reaction solution was cooled to 0° C., and 0.63 g (3.26 mmols) of water-soluble carbodiimide hydrochloride and 0.44 g (3.26 mmols) of HOBt were added thereto. The mixture was stirred for 1 hour while being cooled and then overnight at room temperature. After the reaction mixture was concentrated under reduced pressure, 50 ml of water were added to the residue, and the mixture was extracted twice with 50 ml of ethyl acetate. The organic layer was washed twice with a 5% citric acid aqueous solution, with 50 ml of water, twice with 50 ml of a 5% sodium hydrogencarbonate aqueous solution and with 50 ml of a saturated aqueous solution of sodium chloride. After the organic layer was dried over anhydrous magnesium sulfate, magnesium sulfate was removed by filtration. The filtrate was concentrated under reduced pressure, and was purified with PTLC to obtain N-α-L-(N'-benzyloxycarbonyl-β-O-benzylaspartyl)-(1R,2S,4S)-1-methyl-2-hydroxy-4-phenylhexylamide as a viscous oil.

N-α-L-(N'-benzyloxycarbonyl-β-O-benzylaspartyl)-(1R,2S,4S)-1-methyl-2-hydroxy-4-phenylhexylamide (1.32 g, 2.42 mmols) was dissolved in 40 ml of methanol, and 5 ml of water and 0.85 g of 5% palladium on carbon (water content 50%) were added thereto. The mixed solution was reduced under a hydrogen atmosphere overnight at room temperature. The catalyst was removed by filtration, and the filtrate was concentrated under reduced pressure. The residue was then dried to give 0.72 g (2.23 mmols) of N-α-L-aspartyl-(1R,2S,4S)-1-methyl-2-hydroxy-4-phenylhexylamide (2S:2R=5:1).

$^1$HNMR(DMSO-d$_6$) δ: 0.67(t,3H), 0.99(d,3H), 1.38–1.60 (m,2H), 1.63–1.76(m,2H), 2.53–2.65(m,1H), 2.60–2.80 (2dd,2H), 3.49(m,1H), 3.74(m,1H), 3.94(t,1H), 7.14–7.31 (m,5H), 8.32(d,1H).

ESI-MS 323.2 (MH$^+$).

Degree of sweetness (relative to sugar) 2,500 times.

EXAMPLE 2

Synthesis of N-α-L-aspartyl-(1R,2S,4R)-1-methyl-2-hydroxy-4-phenylhexylamide

Example 1 was repeated except that (S)-2-phenylbutyl bromide was used instead of (R)-2-phenylbutyl bromide to give N-α-L-aspartyl-(1R,2S,4R)-1-methyl-2-hydroxy-4-phenylhexylamide (2S:2R=>9:1) as a solid in a total yield of 54.2%.

$^1$HNMR(DMSO-d$_6$) δ: 0.69(t,3H), 0.93(d,3H), 1.45–1.68 (m,4H), 2.64–2.77(m,3H), 3.10(m,1H), 3.57(m,1H), 3,94(t, 1H), 7.14–7.31(m,5H), 8.28(d,1H).

ESI-MS 322.9 (NH$^+$).

Degree of sweetness (relative to sugar) 1,500 times.

EXAMPLE 3

Synthesis of N-α-L-aspartyl-(1R,2S,4RS)-1-methyl-2-hydroxy-4-phenylhexylamide

Example 1 was repeated except that (RS)-2-phenylbutyl bromide was used instead of (R)-2-phenylbutyl bromide to give N-α-L-aspartyl-(1R,2S,4RS)-1-methyl-2-hydroxy-4-phenylhexylamide as a solid in a total yield of 16.7%.

$^1$NMR(DMSO-d$_6$) δ: 0.66(t,1.5H), 0.70(d,1.5H), 0.93 (d,1.5H), 0.97(d,1.5H), 1.40–1.75(m,4H), 2.10–2.65(m,3H), 3.00(m,0.5H), 3.40(m,0.5H), 3.55–3.90(m,2H), 7.13–7.29 (m,5H), 8.07(brd,0.5H), 8.17(brd,0.5H).

ESI-MS 322.8 (MH$^+$).

Degree of sweetness (relative to sugar) 2,300 times.

EXAMPLE 4

Synthesis of N-α-L-aspartyl-(1R,2S,4RS)-1-methyl-2-hydroxy-4-phenylpentylamide

Example 1 was repeated except that (RS)-2-phenylpropyl bromide was used instead of (R)-2-phenylbutyl bromide to give N-α-L-aspartyl-(1R,2S,4RS)-1-methyl-2-hydroxy-4-phenylpentylamide (2S:2R=7:3) as a solid in a total yield of 29.3%.

$^1$HNMR(DMSO-d$_6$) δ: 0.94(d,1.5H), 1.00(d,1.5H), 1.16 (d,1.5H), 1.18(d,1.5H), 1.46–1.72(m,2H), 2.33–2.60(m,2H), 2.92(m,0.5H), 3.06(m,0.5H), 3.45–3.83(m,2H), 7.12–7.38 (m,5H), 8:14(d,0.5H), 8.24(d,0.5H).

ESI-MS 309.3 (MH$^+$).

Degree of sweetness (relative to sugar) 700 times.

EXAMPLE 5

Synthesis of N-α-L-aspartyl-(1R,2S,4RS )-1-methyl-2-hydroxy-4-phenyl-5-methoxypentylamide Example 1 was repeated except that (RS)-2-phenyl-3-methoxypropyl bromide was used instead of (R)-2- phenylbutyl bromide to give N-α-L-aspartyl-(1R,2S,4RS)-1-methyl-2-hydroxy-4-phenyl-5-methoxypentylamide (2S:2R=7:3) as a solid in a total yield of 34.5%

$^1$HNMR(DMSO-d$_6$) δ: 0.93(d,1.5H), 0.98(d,1.5H), 1.46–1.84(m,2H), 2.68–2.80(m,2H), 2.94–3.22(m,2H), 3.18 (s,3H), 3.29–3.53(m,2H), 3.53–3.78(m,1H), 3.90–4.00(m, 1H), 7.14–7.32(m,5H), 8.30(d,0.5H), 8.39(d,0.5H).

ESI-MS 339.1 (MH$^+$).

Degree of sweetness (relative to sugar) 100 times.

EXAMPLE 6

Synthesis of N-α-L-aspartyl-(1R,2S,4RS)-1-ethyl-2-hydroxy-4-phenylhexylamide

Example 1 was repeated except that (RS)-2-phenylbutyl bromide was used instead of (R)-2-phenylbutyl bromide and N-methoxy-N-methylcarboxyamide of N,N-dibenzyl-α-D-aminobutyric acid instead of N-methoxy-N-methylcarboxyamide of N,N-dibenzyl-α-D-alanine respectively. Consequently, N-α-L-aspartyl-(1R,2S,4RS)-1-ethyl-2-hydroxy-4-phenylhexylamide (2S:2R=>9:1) was obtained as a solid in a total yield of 35.3%.

$^1$HNMR(DMSO-d$_6$) δ: 0.60–0.84(m,6H), 1.15–1.78(m, 6H), 2.33–2.75(m,3H), 2.97(m,1H), 3.45(m,1H), 3.59(m, 1H), 3.77(m,1H), 7.13–7.38(m,5H), 7.95–8.23(brd,1H).

ESI-MS 337.5 (MH$^-$).

Degree of sweetness (relative to sugar) 250 times.

EXAMPLE 7

Synthesis of N-α-L-aspartyl -(1R,2S,4RS)-1-α-hydroxyethyl-2-hydroxy-4-phenylhexylamide Example 1 was repeated except that (RS)-2-phenylbutyl bromide was used instead of (R)-2-phenylbutyl bromide and N-methoxy-N-methylcarboxyamide of N,N-dibenzyl-O-benzyl-α-D-threonine instead of N-methoxy-N-methylcarboxyamide of N,N-dibenzyl-α-D-alanine respectively. Consequently, N-α-L-aspartyl-(1R,2S,4RS)-1-α-hydroxyethyl-2-hydroxy-4-phenylhexylamide (2S:2R=9:1) was obtained as a solid in a total yield of 16.7%.

$^1$HNMR(DMSO-d$_6$) δ: 0.60–0.72(m,3H), 0.82–0.98(m, 3H), 1.30–1.84(m,4H), 2.24–2.40(m,2H), 2.50–2.60(m,1H), 2.66–2.80(m,1H), 2.35–3.65(m,1H), 3.65–3.90(m,1H), 4.00–4.40(m,1H), 7.12–7.34(m,5H), 8.06(brs,1H).

ESI-MS 353.6 (MH$^+$).

Degree of sweetness (relative to sugar) 100 times.

EXAMPLE 8

Synthesis of N-α-L-aspartyl-(1R,2S)-1-methyl-2-hydroxy-4-phenylbutylamide

Example 1 was repeated except that 2-phenylethyl bromide was used instead of (R)-2-phenylbutyl bromide to give N-α-L-aspartyl-(1R,2S)-1-methyl-2-hydroxy-4-phenylbutylamide (2S:2R=9:1) as a solid in a total yield of 28.5%.

$^1$HNMR(DMSO-d$_6$) δ: 1.00(d,3H), 1.46–1.65(m,1H), 1.65–1.73(m,1H), 2.19(dd,1H), 2.39(dd,1H), 2.55–2.60(m, 1H), 2.69–2.80(m,1H), 3.30–3.38(m,1h), 3.58–3.64(m,1H), 3.66–3.74(m,1H)

EST-MS 295.2 (MH$^+$).

Degree of sweetness (relative to sugar) 50 times.

EXAMPLE 9

Synthesis of N-α-L-aspartyl-(1R,2R,4RS)-1-methyl-2-hydroxy-4-phenylhexylamide

LAH (0.40 g, 10.5 mmols) was suspended in 20 ml of ether, and the suspension was maintained at 0° C. To this suspension were added 1.63 g (7.0 mmols) of N-methoxy-N-methylcarboxyamide of N-tert-butoxycarbonyl-α-D-alanine. The mixture was stirred at 0° for 1 hour, and 25 ml of a 1-M potassium hydrogensulfate aqueous solution were added thereto. The reaction solution was extracted twice with 50 ml of ether. The organic layer was washed with 50 ml of a 5% sodium hydrogencarbonate aqueous solution and with a saturated aqueous solution of sodium chloride, and was dried over anhydrous magnesium sulfate. Magnesium sulfate was removed by filtration, and the filtrate was concentrated to obtain 1.21 g (7.0 mmols) of (R)-2-N-tert-butoxycarbonylaminopropyl aldehyde as a solid.

Magnesium (0.63 g, 26.3 mmols) was suspended in 2 ml of THF, and a solution of 3.73 g (17.5 mmols) of (RS)-2-phenylbutyl bromide in 3 ml of THF was added dropwise to the suspension. The reaction solution was stirred at room temperature for 1 hour, and 5 ml of THF were then added thereto. The mixed solution was cooled to −78° C. To the reaction solution was added a solution obtained by dissolving 1.21 g (7.0 mmols) of the above-obtained (R)-2-N-tert-butoxycarbonylaminopropyl aldehyde in 10 ml of THF. The temperature was gradually elevated from −78° C., and the mixture was then stirred at room temperature for 15 hours. To this reaction solution were added 50 ml of a saturated aqueous solution of ammonium chloride, and the mixture was extracted twice with 50 ml of ether. The organic layer was washed with 5% sodium hydrogencarbonate and with a saturated aqueous solution of sodium chloride, and was dried over anhydrous magnesium sulfate. Magnesium sulfate was removed by filtration, and the filtrate was concentrated. The residue was purified with PTLC to obtain 0.91 g (2.96 mmols) of (1R,2S,4RS)-N-tert-butoxycarbonyl-1-methyl-2-hydroxy-4-phenylhexylamine (2S:2R=3:7) as an oil.

Fifteen milliliters of a solution containing 4-N Hcl and dioxane were added to 0.91 g (2.96 mmols) of (1R,2R,4RS)-N-tert-butoxycarbonyl-1-methyl-2-hydroxy-4-phenylhexylamine, and the mixture was stirred at room temperature for 1 hour. The reaction solution was concentrated under reduced pressure, and the residue was further concentrated after the addition of 25 ml of ether. The resulting residue was dissolved was dissolved in 25 ml of methylene chloride. The reaction solution was cooled to 0° C., and 1.17 g (3.26 mmols) of N-benzyloxycarbonyl-L-aspartic acid β-benzyl ester, 0.45 ml (3.26 mmols) of triethylamine, 0.63 g (3.26 mmols) of water-soluble carbodiimide and 0.44 g (3.26 mmols) of HOBt were added thereto. The reaction solution was stirred for 1 hour while being cooled and then overnight at room temperature. After the reaction solution was concentrated under reduced pressure, 50 ml of water were added to the residue, and the resulting solution was extracted twice with 50 ml of a acetate. The organic layer was washed twice with 50 ml of a 5% citric acid aqueous solution, with 50 ml of water, with 50 ml of a 5% sodium hydrogencarbonate aqueous solution and with 50 ml of a saturated aqueous solution of sodium chloride. The organic layer was dried over anhydrous magnesium sulfate, and magnesium sulfate was then removed by filtration. The filtrate was concentrated under reduced pressure, and was purified with PTCL to obtain 1.15 g (2.11 mmols) of N-α-L-(N'-benzyloxycarbonyl-β-O-benzylaspartyl)-(1R,2R,4RS)-1-methyl-2-hydroxy-4-phenylhexylamide as a viscous oil. N-α-L-(N'-benzyloxycarbonyl-β-O-benzylaspartyl)-(1R,2R,4RS)-1-methyl-2-hydroxy-4-phenylhexylamide (1.15 g, 2.11 mmols) was dissolved in 35 ml of methanol, and 5 ml of water and 0.35 g of 5% palladium on carbon (water content 50%) were added thereto. The mixed solution was reduced under a hydrogen atmosphere overnight at room temperature. The catalyst was removed by filtration, and the filtrate was concentrated under reduced pressure. The residue was then dried to give 0.59 g (1.84 mmols) of N-α-L-aspartyl-(1R,2R,4RS)-1-methyl-2-hydroxy-4-phenylhexylamide (2S:2R=3:7) as a solid.

$^1$HNMR(DMSO-d$_6$) δ: 0.67(t, 1.5H), 0.69(t, 1.5H), 0.91 (d, 1.5H)0.96(d, 1.5H), 1.40–1.75(m, 4H), 2.40–2.70(m, 3H, 2.95–3.90 (m, 3H), 7.10–7.35(m, 5H), 8.07(brs, 1H).

ESI MS 323.1 (MH$^+$).

Degree of sweetness (relative to sugar) 1,000 times.

EXAMPLE 10

Synthesis of N-α-L-aspartyl-(1R,2R,4R)-1-methyl-2-hydroxy-4-phenylhexylamide

Example 9 was repeated except that (S)-2-phenylbutyl bromide was used instead of (RS)-2-phenylbutyl bromide to give -N-α-L-aspartyl-1(1R,2R,4R)-1-methyl-2-hydroxy-4-phenylhexylamide (2S:2R=3.7) as a solid in a total yield of 38.6%.

$^1$HNMR(DMSO-d$_6$) δ: 0.58–0.73(m, 3H), 0.88–1.00(m, 3H), 1.35–1.75(m, 4H), 2.45–2.75(m, 3H), 3.05–3.95(m, 3H), 7.13–7.32(m, 5H), 8.07(d, 1H).

ESI-MS 323.1 (MH$^+$).

Degree of sweetness (relative to sugar) 800 times.

EXAMPLE 11

Synthesis of N-α-L-aspartyl-(2RS,4RS)-1,1-dimethyl-2-hydroxy-4-phenylhexylamide

Example 9 was repeated except that N-methoxy-N-methylcarboxyamide of N-tert-butoxycarbonyl-α,α-dimethylglycine was used instead of N-methoxy-N-methylcarboxyamide of N-tert-butoxycarbonyl-α-D-alanine to give N-α-aspartyl-(2RS,4RS)-1,1-dimethyl-2-hydroxy-4-phenylhexylamide as a solid in a total yield of 8.3%.

$^1$HNMR(DMSO-d$_6$) δ: 0.64–0.75(m, 3H), 1.05–1.25(m, 6H), 1.25–1.90(m, 4H), 2.10–2.50(m, 2H), 2.58(m, 1H), 3.05(m, 1H), 3.45–3.90(m, 2h), 7.13–7.30(m, 5h), 7.93(brs, 0.5h), 8.07(brd, 0.5H).

ESI-MS 337.6 (MH$^+$).

Degree of sweetness (relative to sugar) 250 times.

EXAMPLE 12

Synthesis of N-α-L-(N'-3,3-dimethylbutylaspartyl)-(1R,2S,4S)-1-methyl-2-hydroxy-4-phenylhexylamide N-tert-butoxycarbonyl-L-aspartic acid-β-benzyl ester (0.91 g, 2.90 mmols) and 0.58 g (2.80 mmols) of (1R,2S,4S)-1-methyl-2-hydroxy-4-phenylhexylamine (0.558 g, 2.80 mmols) which had been formed as in Example 1 were added to 30 ml of methylene chloride. The reaction solution was cooled to 0° C., and 0.59 g (3.08 mmols) of HOBt were added thereto. The mixed solution was stirred for 1 hour while being cooled and then overnight at room temperature. After the reaction mixture was concentrated under reduced pressure, 50 ml of water were added to the residue, and the mixture was extracted twice with 50 ml of ethyl acetate. The organic layer was washed twice with a 5% citric acid aqueous solution, with 50 ml of water, twice with a 5% sodium hydrogencarbonate aqueous solution and with 50 ml of a saturated aqueous solution of sodium chloride. After the organic layer was dried over anhydrous magnesium sulfate, magnesium sulfate was removed by filtration, and the filtrate was concentrated under reduced pressure to obtain a 1.43 g (2.78 mmols), of N-α-L-(N'-tert-butoxycarbonyl-β-O-benzylaspartyl)-(1R,2S,4S)-1-methyl-2-hydroxy-4-phenylhexylamide as a viscous oil.

Seven milliliters of a solution containing 4-N—HCl and dioxane were added to 1.43 g (2.78 mmols) of N-α-L-(N'-tert-butoxycarbonyl-β-O-benzylaspartyl)-(1R,2S,4S)-1-methyl-2-hydroxy-4-phenylhexylamide, and the mixture was stirred at room temperature for 1 hour. The reaction solution was concentrated under reduced pressure, and 50 ml of a 5% sodium hydrogencarbonate aqueous solution were added to the residue. The mixture was extracted twice with 50 ml of ethyl acetate. The organic layer was washed with a saturated aqueous solution of sodium chloride, and was dried over anhydrous magnesium sulfate. Magnesium sulfate was then removed by filtration, and the filtrate was concentrated under reduced pressure to obtain 1.13 g (2.73 mmols) of N-α-L-(β-O-benzylaspartyl)-(1R,2S,4S)-1-methyl-2-hydroxy-4-phenylhexylamide as a pale yellow oil.

N-α-L-(β-O-benzylaspartyl)-(1R,2S,4S)-1-methyl-2-hydroxy-4-phenylhexylamide (1.13 g, 2.73 mmols) was suspended in 20 ml of THF, and the suspension was maintained at 0° C. To this suspension were added 0.16 ml (2.73 mmols) of acetic acid, 0.34 ml (2.73 mmols) of 3,3-dimethyl butyl aldehyde and 0.87 g (4.10 mmols) of NaB(OAc)$_3$H. The mixture was stirred at 0° C. for 1 hour and then overnight at room temperature. To the reaction solution were added 30 ml of a saturated aqueous solution of sodium hydrogencarbonate, and the mixture was extracted twice with 50 ml of ethyl acetate. The organic layer was washed with a saturated aqueous solution of sodium chloride, and was dried over anhydrous magnesium sulfate. Magnesium sulfate was then removed by filtration, and the filtrate was concentrated under reduced pressure. The residue was purified with PTLC to obtain 1.04 g (2.09 mmols) of N-α-L-(N'-3,3-dimethylbutyl-β-O-benzylaspartyl)-(1R,2S,4 5)-1-methyl-2-hydroxy-4-phenylhexylamide as a pale yellow oil.

N-α-L-(N'-3,3-dimethylbutyl-β-O-benzylaspartyl)-(1R,2S,4S)-1-methyl-2-hydroxy-4-phenylhexylamide (1.04 g, 2.09 mmols) was dissolved in 40 ml of methanol, and 5 ml of water and 0.50 g of 5% palladium on carbon (water content 50%) were added thereto. The solution was reduced under a hydrogen atmosphere overnight at room temperature. The catalyst was removed by filtration, and the filtrate was concentrated under reduced pressure. The residue was then dried to give 0.74 g (1.81 mmols) of N-α-L-(N'-3,3-dimethylbutylaspartyl)-(1R,2s,4S)-1-methyl-2-hydroxy-4-phenylhexylamide (2S:2R=>5:1) as a solid.

$^1$HNMR (DMSO-d$_6$) δ: 0.66(t,3H), 0.83 (s,9H), 1.00 (d,3H), 1.35–1.56(m,4H), 1.63–1.76(m,2H), 2.55–2.72 (m,5H), 3.40–3.48 (m,1H), 3.75–3.88(m,2H), 4.70(brs,1H), 7.10–7.30(m,5H), 3.34(d,1H).

ESI-MS 407.4 (MH$^+$).

Degree of sweetness (relative to sugar) 5,500 times.

EXAMPLE 13

Synthesis of N-α-L-(N'-3,3-dimethylbutylaspartyl)-(1R,2S,4R)-1-methyl-2-hydroxy-4-phenylhexylamide Example 12 was repeated except that (S)-2-phenylbutyl bromide was used instead of (R)-2-phenylbutyl bromide to give N-α-L-(N'-3,3-dimethylbutylaspartyl)-(1R,2S,4R)-1- methyl-2-hydroxy-4-phenylhexylamide (2S:2R=>9:1) as a solid in a total yield of 52.2%.

$^1$HNMR (DMSO-d$_6$) δ: 0.69(t,3H), 0.85(s,9H), 0.93(d, 3H), 1.38–66(m,6H), 2.60–2.78(m,5H), 3.00–3.10(m,1H), 3.58–3.67(m,$_1$H), 3.81(t,1H), 7.10–7.30(m,5H), 4.60 (brs, 1H), 3.26(d, 1H).

ESI-MS 407.4 (MH$^+$).

Degree of sweetness (relative to sugar) 3,000 times.

EXAMPLE 14

Synthesis of N-α-L-(N'-2-ethylbutylaspartyl-(1R,2S, 4S)-1-methyl-2-hydroxy-4-phenylhexylamide Example 12 was repeated except that 2-ethylbutyl aldehyde was used instead of 3,3-dimethylbutyl aldehyde to give N-α-L-(N'-2-ethylbutylaspartyl)-(1R,2S,4S)-1-methyl-2-hydroxy-4-phenylhexylamide as a solid in a total yield of 30.6%.

$^1$HNMR (DMSO-d$_6$) δ: 0.66(t,3H), 0.79(t,6H), 1.00(d, 3H), 1.22–1.36(m,4H), 1.36–1.54(m,3H), 1.64–1.77(m,2H), 2.50–2.66(m,5H), 3.38(brs,1H), 3.67(t,1H), 3.73–3.83(m, 1H), 4.66(brs,1H), 7.10–7.23(m,5H), 8.17(d,1H).

ESI-MS 407.4 (MH$^+$).

Degree of sweetness (relative to sugar) 3,000 times.

EXAMPLE 15

Synthesis of N-α-L-(N'-3-methylbutylaspartyl)-(1R, 2S,4S )-1-methyl-2-hydroxy-4-phenylhexylamide Example 12 was repeated except that 3-methylbutyl aldehyde was used instead of 3,3-dimethylbutyl aldehyde to given N-α-L-(N'-3-ethylbutylaspartyl)-(1R,2S,4S)-1-methyl-2-hydroxy-4-phenylhexylamide as a solid in a total yield of 25.4%.

$^1$HNMR (DMSO-d$_6$) δ: 0.66(t,3H), 0.83(d,3H), 0.84(d, 3H), 1.00(d,3H), 1.30–1.62(m,5H), 1.62–1.76(m,2H), 2.40–2.54(m,3H), 2.60(t,2H), 3.34–3.44(m,1H), 3.64(t,1H), 3.70–3.80(m,1H), 4.67(brs,1H), 7.12–7.32(m,5H), 8.14(d, 1H).

ESI-MS 393.4 (MH$^+$).

Degree of sweetness (relative to sugar) 4,000 times.

EXAMPLE 16

Synthesis of N-α-L-(N'-3,3-dimethylbutylaspartyl)-(1R,2S)-1-methyl-2-hydroxy-3-cyclohexylpropylamide Example 12 was repeated except that cyclohexylmethyl bromide was used instead of (R)-2-phenylbutyl bromide to give N'-L-(N'-3,3-dimethylbutylaspartyl)-(1R,2S)-1methyl-2-hydroxy-3-cyclohexylpropylamide as a solide in a total yield of 11.3%

$^1$HNMR (DMSO-d$_6$) δ: 0.88(s,9H), 0.99(d,3H), 0.80–1.80 (m,15H), 2.60(d,2H), 2.69(t,2H), 3.41–3.48)(m, 1), 3.62–3.72(m,1H), 3.77(t,1H), 4.57(brs,1H), 8.25(d,1H).

ESI-MS 371.4 (MH$^+$).

Degree of sweetness (relative to sugar) 100 times.

EXAMPLE 17

Synthesis of N-α-L-(N'-3,3-dimethylbutylaspartyl)-(1R,2R)-1-methyl-2-hydroxy-3-cyclohexylpropylamide)

LAH (0.66 g, 17.5 mmols) was suspended in 40 ml of ether, and the suspension was maintained at 0° C. To this suspension was added 2.32 g (10.0 mmols) of N-methoxy-N-methylcarboxyamide of N-tert-butoxycarbonyl-α-D-alanine. The mixture was stirred at 0° C. for 1 hour, and 25 ml of a 1-M potassium hydrogensulfate aqueous solution were then added thereto. The reaction solution was extracted twice with 50 ml of ether. The organic layer was washed with 50 ml of a 5% sodium hydrogencarbonate aqueous solution and with a saturated aqueous solution of sodium chloride, and was dried over anhydrous magnesium sulfate. Magnesium sulfate was removed by filtration, and the filtrate was concentrated to obtain 1.29 g (7.43 mmols) of (R)-2-N-tertbutoxycarbonylaminopropyl aldehyde in 10 ml of THF. The temperature was gradually elevated from −78° C., and the mixture was then stirred at room temperature for 15 hours. To this reaction solution were added 50 ml of a saturated aqueous solution of ammonium chloride, and the mixture was extracted twice with 50 ml of ether. The organic layer was washed with 5% sodium hydrogencarbonate and with a saturated aqueous solution of sodium chloride, and was dried over anhydrous magnesium sulfate. Magnesium sulfate was removed by filtration, and the filtrate was concentrated. The residue was purified with PTLC to obtain 0.88 g (3.25 mmols) of (1R,2R)-N-tert-butoxycarbonyl-1-methyl-2-hydroxy-3-cyclohexylpropylamine (2S:2R=3:7) as an oil.

Fifteen milliliters of a solution containing 4-N HCl and dioxane were added to 0.88 g (3.25 mmols) of (1R,2R)-N-tert-butoxycarbonyl-1-methyl-2-hydroxypropylamine, and the mixture was stirred at room temperature for 1 hour. The reaction solution was concentrated under reduced pressure, and the residue was further concentrated after the addition of 25 ml of ether. The resulting residue was dissolved in 30 ml of methylene chloride, and the solution was cooled to 0° C. N-tert-butoxycoarbonyl-L-aspartic acid-β-benzyl ester 1.11 (3.42 mmols), 0.50 ml (3.58 mmols) of triethylamine, 0.69 g (3.S8 mmols) of water-soluble carbodiimide and 0.48 g (3.58 mmols) of HOBt were added to the above-obtained solution. The mixture was stirred for 1 hour while being cooled and then overnight at room temperature. After the reaction solution was concentrated under reduced pressure, 50 ml of water were added to the residue, and the mixture was extracted twice with 50 ml of ethyl acetate. The organic layer was washed twice with 50 ml of a 5% citric acid aqueous solution, with 50 ml of water, twice with a 5% sodium hydrogencarbonate aqueous solution and with 50 ml of a saturated aqueous solution of sodium chloride. The organic layer was dried over anhydrous magnesium sulfate, and magnesium sulfate was then removed by filtration. The filtrate was concentrated under reduced pressure, and was purified through PTLC to obtain 0.81 g (1.69 mmols) of N-α-L-(N'-tert-butoxycarbonyl-β-O-benzylaspartyl)-(1R, 2R)-1-methyl-2-hydroxy-3-cyclohexylpropylamide as a viscous oil.

Eight milliliters of a solution containing 4-N HCl and dioxane were added to 0.81 g (1.69 mmols) of N-α-L-(N'-tert-butoxycarbonyl-β-O-benzylaspartyl)-(1R,2R)-methyl-2-hydroxy-3-cyclohexylpropylamide, and the mixture was stored at room temperature for 1 hour. The reaction solution was concentrated under reduced pressure, and 50 ml of a sodium hydrogencarbonate aqueous solution were added to the residue. The mixture was extracted twice with 50 ml of ethyl acetate. The organic layer was washed with a saturated aqueous solution of sodium chloride, and was dried over anhydrous magnesium sulfate. Magnesium sulfate was then removed by filtration, and the filtrate was concentrated under reduced pressure to obtain 0.60 g (1.60 mmols) of N-,α-L-(β-O-benzylaspartyl)-(1R,2R)-1-methyl-2-hydroxy-3-cyclohexylpropylamide as a sale yellow viscous oil.

N-α-L-(β-O-benzylaspartyl)-(1R,2R)-1-methyl-2-hydroxy-3-cyclohexylpropylamide (0.60 g, 1.60 mmols) was suspended in 12 ml of THF, and the suspension was maintained at 0° C. To this suspension were added 0.092 ml (1.60 mmols) of acetic acid, ID.20 ml (1.60 mmols) of 3,3-dimethylbutyl aldehyde and 0.51 g (2.41 mmols) of NaB(OAc)$_3$H. The mixture was stirred at 0° C. for 1 hour and then overnight at room temperature. Twenty milliliters of a saturated aqueous solution of sodium hydrogencarbonate were added to the reaction solution, and the mixture was extracted twice with 50 ml of ethyl acetate. The organic layer was washed with a saturated aqueous solution of sodium chloride, and was dried over anhydrous magnesium sulfate. Magnesium sulfate was then removed by filtration, and the filtrate was concentrated under reduced pressure. The residue was purified with PTLC to obtain 0.50 g (1.09 mmols) of N-α-L-(N'-3,3-dimethylbutyl-β-O-benzylaspartyl)-(1R,2R)-1-methyl-2-hydroxy-3-cyclohexylpropylamide as a pale yellow oil.

N-α-L-(N'-3,3-dimethylbutyl-β-O-benzylaspartyl)-(1R,2R)-1-methyl-2-hydroxy-3-cyclohexylpropylamide (0.50 g, mmols) was dissolved in 30 ml of methanol, and 5 ml of water and 0.25 g of 5% palladium on carbon (water content-50%) were added thereto. The solution was reduced under a hydrogen atmosphere at room temperature for 4 hours, catalyst was removed by filtration, and the filtrate w concentrated under reduced pressure. The residue was then dried to give 0.36 g (0.98 mmols) of N-α-L-(N'-3,3-dimethylbutylaspartyl)-(1R,2R)-1-methyl-2-hydroxy-3cyclohexylpropylamide as a solid.

$^1$HNMP$_r$(DMSO-d$_6$) δ: 0.86(s,9H), 1.02(d,3H), 0.80–1.74 (m,15H), 2.48–2.56(m,2H), 2.60–2.70(m,2H), 3.40–3.55(m, 1H), 3.63–3.83(m,2H), 4.53(brs,1H), 8.06(d,1H).

ESI-MS 371.4 (MH$^+$).

Degree of sweetness (relative to sugar) 750 times.

The disclosure of Japan priority patent application Nos. 003651/1996, filed Jan. 12, 1996; 078718/1996, filed Apr. 1, 1996; and 291501/1996, filed Nov. 1, 1996, are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. Novel aspartylamide derivatives represented by formula (I)

R$_1$—NHC$^1$H(CH$_2$COOH)CONH—C$^2$R$_2$R$_3$—C$^3$H(OH)—R$_4$ (I)

wherein
R$_1$ represents H, or a hydrocarbon group selected from the group consisting of 3,3-dimethyl butyl, 2-ethyl butyl and 3-methyl butyl;

R$_2$ and R$_3$ each represent H, or a substituent selected from an alkyl group having from 1 to 6 carbon atoms, an alkoxyalkyl group having from 2 to 7 carbon atoms, a hydroxyalkyl group having from 2 to 7 carbon atoms, a phenyl group, and a 2-furyl group, or R$_2$ and R$_3$ taken together with the carbon to which they are attached form a cycloalkyl group containing 3 to 6 carbon atoms;

when R$_1$ is said hydrocarbon group, R$_4$ represents an alkyl group having from 1 to 12 carbon atoms, or a substituent represented by formula (II) or (III), and when R$_1$ is H, R$_4$ represents a substituent represented by formula (III)

—(CHR$_5$)$_n$—R$_6$ (II)

—(CH$_2$)$_m$C$^4$HR$_7$R$_8$ (III)

in which
in formula (II)
R$_5$ represents H, or an alkyl group having from 1 to 4 carbon atoms,
R$_6$ represents a cyclic group containing up to 10 ring carbon atoms and up to 12 total carbon atoms, which cyclic group is cycloalkyl, cycloalkenyl, lower alkyl substituted cycloalkyl or cycloalkenyl, bicycloalkyl, bicycloalkenyl, or tricycloalkyl, and
n represents 0 or 1, and
in formula (III)
R$_7$ and R$_8$ each represent H; a cycloalkyl group having from 3 to 4 carbon atoms; an alkyl group having from 1 to 6 carbon atoms; an alkoxyalkyl group having from 2 to 7 carbon atoms; a phenyl group; a phenyl group having a substituent selected from F, Cl, Br, I, a hydroxy group, an alkyl group having from 1 to 6 carbon atoms, an alkoxy group having from 2 to 7 carbon atoms, a cyano group, a nitro group, an acetyl group, an amino group and an acetylamino group in the 2-, 3- or 4-position; a phenyl group having a methylenedioxy group, a trimethylene group or a tetramethylene group in the 2- and 3-positions or in the 3- and 4-positions; a 2-, 3- or 4-pyridyl group; a 2- or 3-furyl group; or a 2- or 3-thienyl group, and
m represents 0 or 1; and
the C$^1$-configuration is (S), and the C$^2$-, C$^3$- and C$^4$-configurations are (R), (S) or (RS), and salts thereof, wherein when R$_1$ is H, R$_4$ as formula (III) is not alkyl or cycloalkyl.

2. The compounds of claim 1, wherein R$_1$ is H, R$_2$ is H, R$_3$ is a methyl group, R$_4$ is a (S)-, (R)- or (RS)-2-phenylbutyl group, the C$^2$-configuration is (R), and the C$^3$-configuration is (S), (R) or (RS).

3. The compounds of claim 1, wherein R$_1$ is H, R$_2$ is H, R$_3$ is a methyl group, R$_4$ is a (S)-, (R)- or (RS)-2-phenylpropyl group, the C$^2$-configuration is (R), and the C$^3$-configuration is (S), (R) or (RS).

4. The compounds of claim 1, wherein R$_1$ is H, R$_2$ is H, R$_3$ is a methyl group, R$_4$ is a (S)-, (R)- or (RS)-2-phenyl-3-methoxypropyl group, the C$^2$-configuration is (R), and the C$^3$-configuration is (S), (R) or (RS).

5. The compounds of claim 1, wherein R$_1$ is H, R$_2$ is H, R$_3$ is an ethyl group, R$_4$ is a (S)-, (R)- or (RS)-2-phenylbutyl group, the C$^2$-configuration is (R), and the C$^3$-configuration is (S), (R) or (RS).

6. The compounds of claim 1, wherein R$^1$ is H, R$_2$ is H, R$_3$ is a 1-hydroxyethyl group, R$_4$ is a (S)-, (R)- or (RS)-2-phenylbutyl group, the C$^2$-configuration is (R), and the C$^3$-configuration is (S), (R) or (RS).

7. The compounds of claim 1, wherein R$_1$ is H, R$_2$ and R$_3$ are methyl groups, R$_4$ is a (S)-, (R)- or (RS)-2-phenylbutyl group, and the C$^3$-configuration is (S), (R) or (RS).

8. The compounds of claim 1, wherein R$_1$ is H, R$_2$ is H, R$_3$ is a methyl group, R$_4$ is a 2-phenylethyl group, the C$^2$-configuration is (R), and the C$^3$-configuration is (S), (R) or (RS).

9. The compounds of claim 1, wherein R$_1$ is a 3,3-dimethylbutyl group, R$_2$ is H, R$_3$ is a methyl group, R$_4$ is a (S)-, (R)- or (RS)-2-phenylbutyl group, the C$^2$-configuration is (R), and the C$^3$-configuration is (S), (R) or (RS).

10. The compounds of claim 1, wherein R$_1$ is a 2-ethylbutyl group, R$_2$ is H, R$_3$ is a methyl group, R$_4$ is a (S)-, (R)- or (RS)-2-phenylbutyl group, the $C^2$-configuration is (R), and the $C^3$-configuration is (S), (R) or (RS).

11. The compounds of claim 1, wherein $R_1$ is a 3-methylbutyl group, $R_2$ is H, $R_3$ is a methyl group, $R_4$ is a (S)-, (R)- or (RS)-2-phenylbutyl group, the $C^2$-configuration is (R), and the $C^3$-configuration is (S), (R) or (RS).

12. The compounds of claim 1, wherein $R_1$ is 3,3-dimethylbutyl group, $R_2$ is H, $R_3$ is a methyl group, $R_4$ is a cyclohexylmethyl group, the $C^2$-configuration is (R), and the $C^3$-configuration is (S), (R) or (RS).

13. A sweetener containing the novel aspartylamide derivatives of formula (I) or salts thereof of claim 1 as an active ingredient.

* * * * *